US010092190B2

(12) United States Patent
Rege et al.

(10) Patent No.: US 10,092,190 B2
(45) Date of Patent: *Oct. 9, 2018

(54) MULTIMODAL LASER SPECKLE IMAGING

(71) Applicant: THE JOHNS HOPKINS UNIVERSITY, Baltimore, MD (US)

(72) Inventors: Abhishek Rege, Baltimore, MD (US); Nitish Thakor, Clarksville, MD (US); Kartikeya Murari, Calgary (CA); Nan Li, Arlington, MA (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 384 days.

This patent is subject to a terminal disclaimer.

(21) Appl. No.: 14/879,260

(22) Filed: Oct. 9, 2015

(65) Prior Publication Data

US 2016/0113504 A1 Apr. 28, 2016

Related U.S. Application Data

(63) Continuation-in-part of application No. 13/394,261, filed as application No. PCT/US2010/047949 on Sep. 7, 2010, now Pat. No. 9,155,480.

(Continued)

(51) Int. Cl.
*H04N 7/18* (2006.01)
*H04N 9/43* (2006.01)
(Continued)

(52) U.S. Cl.
CPC .......... *A61B 5/0075* (2013.01); *A61B 5/0035* (2013.01); *A61B 5/0062* (2013.01);
(Continued)

(58) Field of Classification Search
None
See application file for complete search history.

(56) References Cited

U.S. PATENT DOCUMENTS

| 5,934,278 A | 8/1999 | Ishihara et al. |
| RE44,042 E * | 3/2013 | Yun ..................... G01N 21/4795 356/479 |

(Continued)

FOREIGN PATENT DOCUMENTS

WO 2009008745 A2 1/2009

OTHER PUBLICATIONS

Murari, K., et al.; "Contrast-enhanced imaging of cerebral vasculature with laser speckle;" Applied Optics, vol. 46, No. 22, Aug. 1, 2007, pp. 5340-5346.

(Continued)

*Primary Examiner* — Andy Rao
*Assistant Examiner* — Samuel D Fereja
(74) *Attorney, Agent, or Firm* — Gianna J. Arnold; Saul Ewing Arnstein & Lehr LLP

(57) ABSTRACT

A system for multimodal laser speckle imaging may include a first light source positioned to emit laser light toward a target, a second light source positioned to emit light toward the target, a camera positioned to receive light scattered from the target, and a processor. The processor may be programmed to receive from the at least one camera at least one image of the target as illuminated by the laser, obtain a laser speckle contrast image of the target from the at least one image of the target as illuminated by the laser, receive from the at least one camera at least one image of the target as illuminated by the second light source, divide the laser speckle contrast image into subparts, and divide the at least one image of the target as illuminated by the second light source into identical subparts, determine whether each subpart includes a feature of a certain type by combining each subpart of the laser speckle contrast image with the at least one image of the target as illuminated by the second light source and comparing the combination with one or more (Continued)

Methodology of feature extraction as pertains to arteriole/venule classification criteria, and out-putting the location and type of features detected in a subpart of the images.

23 Claims, 7 Drawing Sheets

Related U.S. Application Data

(60) Provisional application No. 61/239,947, filed on Sep. 4, 2009.

(51) Int. Cl.
    *H04N 13/04*     (2006.01)
    *A61B 5/00*     (2006.01)
    *A61B 5/026*     (2006.01)

(52) U.S. Cl.
    CPC ............ *A61B 5/0261* (2013.01); *A61B 5/489* (2013.01); *A61B 2576/00* (2013.01)

(56) References Cited

U.S. PATENT DOCUMENTS

| | | |
|---|---|---|
| 2005/0143662 A1 | 6/2005 | Marchitto et al. |
| 2008/0262359 A1 | 10/2008 | Tearney et al. |
| 2010/0189313 A1 | 7/2010 | Prokoski |
| 2011/0013002 A1 | 1/2011 | Thompson et al. |

OTHER PUBLICATIONS

Dunn, Andrew K., et al.; Spatial Extent of Oxygen Metabolism and Hemodynamic Changes During Functional Activation of the Rat Somatosensory Cortex; Elsevier; NeuroImage 27 (2005) 279-290.

* cited by examiner

Multimodal laser speckle imaging on the bench top

Portable Device

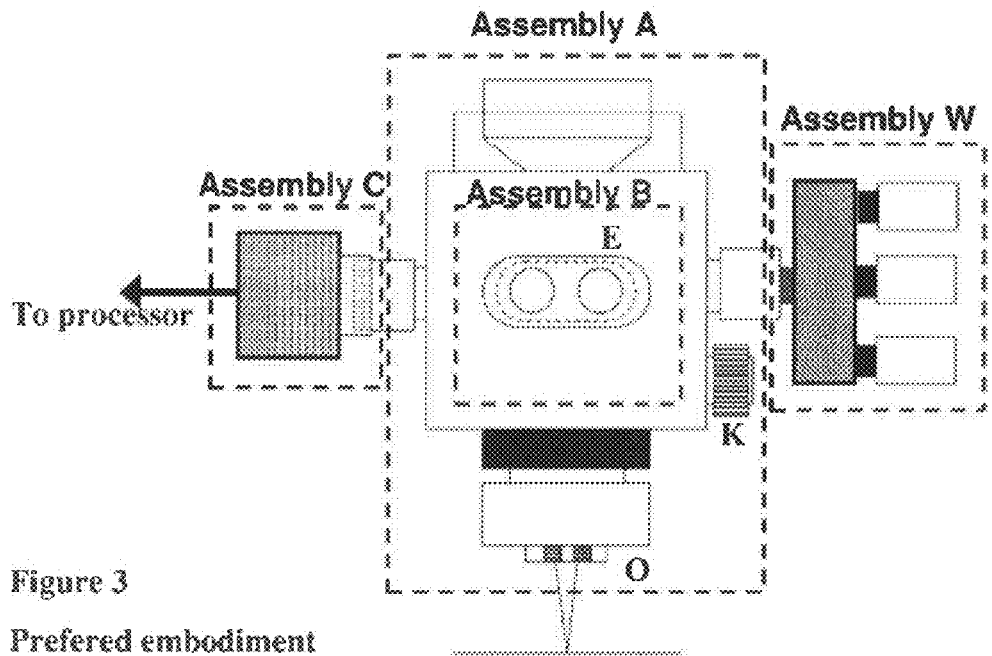

Figure 3

Prefered embodiment for intraoperative use

Assembly A: A conventional surgical microscope

Assembly B: Modified optics (an arrangement of lens, mirrors, apertures and filters) for light focusing on target and image acquisition by camera Assembly C: Camera with associated optical elements such as aperture and shutter control Assembly W: Illumination Wheel with multiple illumination sources mounted, complete with necessary filters and focusing optics E: Eyepiece     K: Magnification knob     O: Objective lens
T: Target Tissue Methodology of feature extraction as pertains to arteriole/venule classification Multi exposure laser speckle imaging Methodology of flow estimation Methodology of feature edge extraction as pertains to arteriole/venule calculation and indication

MULTIMODAL LASER SPECKLE IMAGING

CROSS-REFERENCE TO RELATED APPLICATIONS

This application is a continuation-in-part of and claims priority to U.S. application Ser. No. 13/394,261, filed Mar. 5, 2012, which claims priority to and the benefit of PCT/US2010/047949, filed Sep. 7, 2010 and U.S. Provisional Application No 61/239,947, filed Sep. 4, 2009, the entire contents of which are fully incorporated herein by reference.

BACKGROUND

Laser speckle (LS) imaging is a well known technique. A laser speckle image is obtained by imaging coherent light scattered from a target. If the target includes scatterers at a variety of different depths, the scattering will cause the originally coherent light to add constructively or destructively depending on the various path lengths from the various scatterers, resulting in an image with bright and dark spots, i.e., speckles. The speckle pattern will change if the scatterers are moving. Thus a laser speckle contrast image will tend to have lower contrast in areas where the scatterers are moving and smearing the speckle pattern. A laser speckle contrast image can be calculated based on one or more raw laser speckle images like this:

$$K(x, y) = \frac{\sigma_N[I(i, j)]}{\mu_N[I(i, j)]} \forall (i, j) \in S$$

where i indexes the rows of the image, j indexes the columns of the image N is the number of raw laser speckle images being combined. I represents the intensity in an acquired raw laser speckle image, S represents either a single pixel (i,j) in several images across time or a limited region of the raw image around (i, j) in a single image such as a [5 pixel×5 pixel] window, $\sigma$ represents the standard deviation of intensity I calculated either over S within a single image or at a single pixel over images, $\mu$ represents the mean of the intensity I calculated either over S within a single frame or a single pixel over N images, and K(x,y) is the calculated laser speckle contrast at pixel (x,y) of the LS image.

The LS image can be used to calculate blood flow using the following equation:

$$K^2 = \frac{\tau_c}{2T}\left(1 - \exp\left(\frac{-2T}{\tau_c}\right)\right)$$

where K is the LS contrast, T is the exposure time over which images are acquired, and $1/\tau_c$ is an indicator of blood flow speed.

SUMMARY

The following presents a simplified summary in order to provide a basic understanding of some aspects of the invention. This summary is not an extensive overview of the invention. It is not intended to identify key/critical elements of the invention or to delineate the scope of the invention. Its sole purpose is to present some concepts of the invention in a simplified form as a prelude to the more detailed description that is presented later.

A system for multimodal laser speckle imaging may include a first light source positioned to emit laser light toward a target, a second light source positioned to emit light toward the target, a camera positioned to receive light scattered from the target, and a processor. The processor may be programmed to receive from the at least one camera at least one image of the target as illuminated by the laser, obtain a laser speckle contrast image of the target from the at least one image of the target as illuminated by the laser, receive from the at least one camera at least one image of the target as illuminated by the second light source, divide the laser speckle contrast image into subparts, and divide the at least one image of the target as illuminated by the second light source into identical subparts, determine whether each subpart includes a feature of a certain type by combining each subpart of the laser speckle contrast image with the at least one image of the target as illuminated by the second light source and comparing the combination with one or more criteria, and outputting the location and type of features detected in a subpart of the images.

BRIEF DESCRIPTION OF THE DRAWINGS

For a more complete understanding of the nature and desired objects of the present invention, reference is made to the following detailed description taken in conjunction with the accompanying drawing figures wherein like reference characters denote corresponding parts throughout the several views.

FIGS. 1-3 show exemplary systems carrying out the techniques described herein.

DETAILED DESCRIPTION

Figure 1:
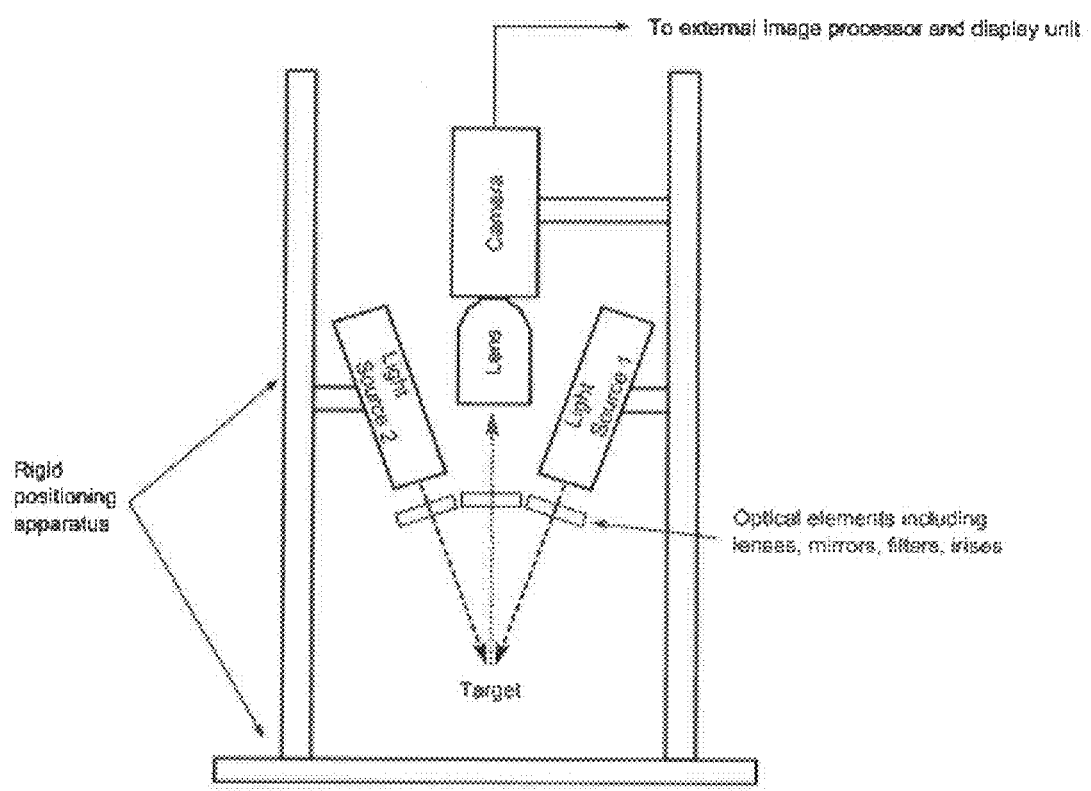

A system for multimodal laser speckle imaging may include: a first light source positioned to emit laser light toward a target; a second light source positioned to emit light toward the target; at least one camera positioned to receive light scattered from the target; and a processor programmed to: receive from the at least one camera at least one image of the target as illuminated by the laser; from the at least one image of the target as illuminated by the laser, obtain a laser speckle contrast image of the target (e.g., as per Equation 1); receive from the at least one camera at least one image of the target as illuminated by the second light source; divide the laser speckle contrast image into subparts, and divide the at least one image of the target as illuminated by the second light source into identical subparts; determine Whether each subpart includes a feature of a certain type by combining each subpart of the laser speckle contrast image with the at least one image of the target as illuminated by the second light source and comparing the combination with one or more criteria; and outputting the location and type of features detected in a subpart of the images.

The target may include in vivo vasculature, including but not limited to brain, eye or skin vasculature. In alternative embodiments, the target may include vasculature located within any tissue of the human or animal body, individual vessels, or a network of connected vessels. The target may further include a system of enclosed tubes with particulates material flowing through them. For example, the target may be a plastic tube with artificial blood flowing through it, or the target may be microfluidic channels with cells or microbeads flowing through them.

The processor may be further programmed to: based on one or both of the laser speckle contrast image of the target and the at least one image of the target as illuminated by the second light source, obtain a feature mask; and prior to dividing the laser speckle contrast image into subparts, mask the laser speckle contrast image and the at least one image of the target as illuminated by the second light source. Obtaining the feature mask may comprise comparing the laser speckle contrast image of the target and the at least one image of the target as illuminated by the second light source to a criterion preselected to correspond to vascular features.

The criterion or criteria to which the combination is compared may be predetermined to distinguish arterial vessels and the blood flow therein from venous vessels and the blood flow therein. Combining the laser speckle contrast image and the image of the target as illuminated by the second light source may comprise digital subtraction including subtracting the result of a mathematical function of the values in the laser speckle contrast image from the result of a mathematical function of the values in the at least one image of the target as illuminated by the second light source. The mathematical functions may be polynomial functions in which the image values are each multiplied by a constant and raised to an exponent.

The processor may be further programmed to: determine a blood flow speed at a particular location in the masked laser speckle contrast image; and output the blood flow speed and the corresponding location.

The processor may be further programmed to: receive from the camera multiple images of the target as illuminated by the laser at multiple different exposure times; and from the multiple images of the target as illuminated by the laser, obtain multiple laser speckle contrast images, each corresponding to a different exposure time.

The second light source may emit laser light or non-coherent light, which may be of a different wavelength than the laser light emitted by the first light source.

The processor may be further programmed to: calculate and output the amount of blood flowing in a detected feature based on an analysis of the feature in the laser speckle contrast image.

The processor may be further programmed to calculate and output the amount of blood flowing in a detected feature as a function of position within the detected feature.

The system may obtain the laser speckle contrast image of the target by combining a plurality of laser speckle contrast images of the target having a plurality of exposure times.

The system may include a camera with light detectors made using complementary metal oxide semiconductor (CMOS) technology or charge coupled device (CM) technology or any other electronic or non-electronic detector. The system may include a laser emitting diode, a HeNe laser, or any other sort of coherent light source. The system may also include sources of white or colored non-coherent light.

In addition, the system may comprise a display module, the function of which is to make the acquired and processed data available for viewing to the user of the system. Examples of display module include but are not limited to computer monitors, printers, screens of phone or tablet computing devices. One or more similar or dissimilar display modules may be used.

In addition, the system may comprise a storage module, the function of which is to store the acquired and processed data for short or long term use. Examples of storage modules include but are not limited to hard disks, solid state disks, and flash memory. The storage module may be connected to the system through wired interfaces such as USB (universal serial bus), firewire, serial or parallel ATA, and ethernet; or through wireless interfaces such as Bluetooth, near field communication (NFC), or internet protocols. Accordingly, the storage module may be located in close physical proximity to the remainder of the system, or be located remote, such as in the case of cloud storage devices and services. One or more similar or dissimilar storage modules and services may be used.

The processor may be programmed to utilize an edge-detection algorithm to calculate a displayable map of arterial or venous blood flow in the target. The processor may also be programmed to skeletonize the calculated map. Skeletonizing a map of vessels typically involves associating with each feature a depiction of the feature that is one-pixel thick.

The systems and methods described herein may be used to distinguish arterioles from venules. Arterioles look darker than venules in LS contrast images due to the higher blood velocity through them. Arterioles also look lighter than venules in white light (WL) reflectance images since they carry oxygenated blood (giving them a bright reddish appearance). Thus, in one embodiment, those vessels having intensities lower than a threshold in LS contrast images and simultaneously having intensities higher than another threshold in the WL reflectance images, can be identified as arterioles. Image preprocessing involving smoothing and contrast enhancement can be done before this comparison for segmentation (i.e., distinction) of vessels from the background. Such pre-processing can involve many different possible methods including Gaussian smoothing, median filters, histogram equalization, ridge detection, ridge tracking or region growing methods. Discrimination between arterioles and venules can be done for all sizes of blood vessels from bigger arteries and veins to the smallest of arterioles and venules in any organ of the human or animal body.

The systems and methods described herein may be used to determine the distribution of flow in individual microvessels within branching networks, potentially over a wide field of view. This can be done for any vessel and any branch point in the field of view, thereby providing an advantage over higher resolution scanning techniques such as two photon microscopy. Flow distribution can be obtained in vessels of all sizes (from bigger arterioles and venules to smallest sized capillaries). Elucidation of flow distribution within vessels provides an advantage over regional blood flow imaging techniques.

The systems and methods described herein can improve accuracy and dynamic range of laser speckle imaging to enable consistent measurements across longitudinal assessment or different subjects using multi-expo sure LSI. The use of LSI in longitudinal assessment of vascular changes (for example, over days) has suffered because the technique is susceptible to errors due to differing experimental preparation. This problem translates to not being able to consistently and reliably relate the flows observed in different patients or in the same patient at different times. In the laboratory, variables such as illumination conditions and animal preparation may change despite the best standardization efforts, that is, preparation in animal models for brain vessel imaging is subject to day to day variability. This adversely affects longitudinal flow studies where the same animal is monitored on multiple days. A modified laser speckle imaging method described here is based on multi-exposure recording that is robust to day-to-day environmental changes and improves the sensitivity of flow measurement over a wider range of blood flow values. The method involves acquisition of raw laser speckle imaging at multiple exposures and processing them together so to extract the change of speckle from one exposure to another. This metric is more robust to day-to-day changes, thereby providing a better estimate of flows.

The systems and methods described herein may be used to distinguish subsurface vessels by using multiple wavelengths of incident light for LSI. For example, currently, there is a gap in the understanding of the role of meningeal and cortical vessels in many neuroscience studies, such as migraines. Further, depth of the vessels to be imaged has an influence on the image produced using any optical modality. Thus, images can only be accurate to a point. Multiple wavelengths may be used in the present methods to deconvolve the confounding effects of depth. For example, it is possible to distinguish between dural and cortico-pial vessels (of the brain) using LSI sequentially under green and red laser illumination. Comparing the relative intensities obtained at different wavelengths, it is possible to incorporate a depth correction into the technique.

The systems and methods described herein may be implemented in portable devices, and they may be used without restraining the subject. For example, laser speckle and associated calculations may be implemented on an electronic chip using very large scale integration (VLSI) or field programmable gate array (FPGA) technology. Traditional laser speckle imaging requires the processing capabilities of fast computers. The present processing methodologies may be implemented on VLSI or FPGA chips or a combination of the two. All components of the imaging system—the illumination, the optics, the image acquisition and image processing—may be performed in an integrated device. Advances in miniaturization and integrated circuit technology help make this possible. Light Emitting Diodes (LEDs) and Laser Diodes are available in small footprint packages with excellent control over wavelength, stability and power output. Solid state image sensors are widely used in the medical and biomedical fields for diagnostic and research imaging. Complementary Metal Oxide Semiconductor (CMOS) circuit technology has also developed to a point where it is possible to implement image processing algorithms on the image plane on silicon.

In one embodiment as shown in FIG. 1, the system includes at least one laser light source and white or colored light sources with an optics assembly to illuminate the region of interest, an acquisition system of camera and an optics assembly to image the same region, a data processing system and possibly a display system to show the extracted information to a user.

One or two laser sources are used to illuminate the region of interest (for example, a region of thinned skull over the cortex of a rat). Typical lasers used are a red HeNe gas laser of wavelength 632 nm and a green diode pumped solid-state (DPSS) laser of wavelength 532 nm. A white-light source, such as a DC powered halogen, is used to illuminate the same region with white light. Through an array of optics which include arrangements of lenses, mirrors, beam splitters, beam attenuators/diffusers and aperture control elements, the beams from all the illumination sources are directed to the region of interest, FIG. 1 shows one such arrangement. Each illumination source is independently controlled by an ON/OFF switch which is used to selectively turn ON or OFF each source in any desired order.

In this embodiment, image acquisition is done using a camera system. This preferred embodiment uses a 12 bit cooled SVGA CCD camera with a pixel size of 6.7 µm×6.7 µm (for a 1:1 magnification) and shutter control. An assembly of optics can be used to appropriately magnify the region of interest and control the effective aperture through which light is collected by the camera system. Such an optics assembly can include lens systems with aperture control, mirrors and beam splitters. Thus, an image of the region of interest can be projected on the camera sensor through an adjustable timing shutter. In the preferred embodiment, a stack of 80 images of the same region is acquired sequentially in time under each type of illumination. This number of images in the time-stack is empirical and the preferred embodiment uses an empirically proven optimum of 80 images, it suffices to acquire a time-stack of only 5 images under WL illumination.

Figure 2:
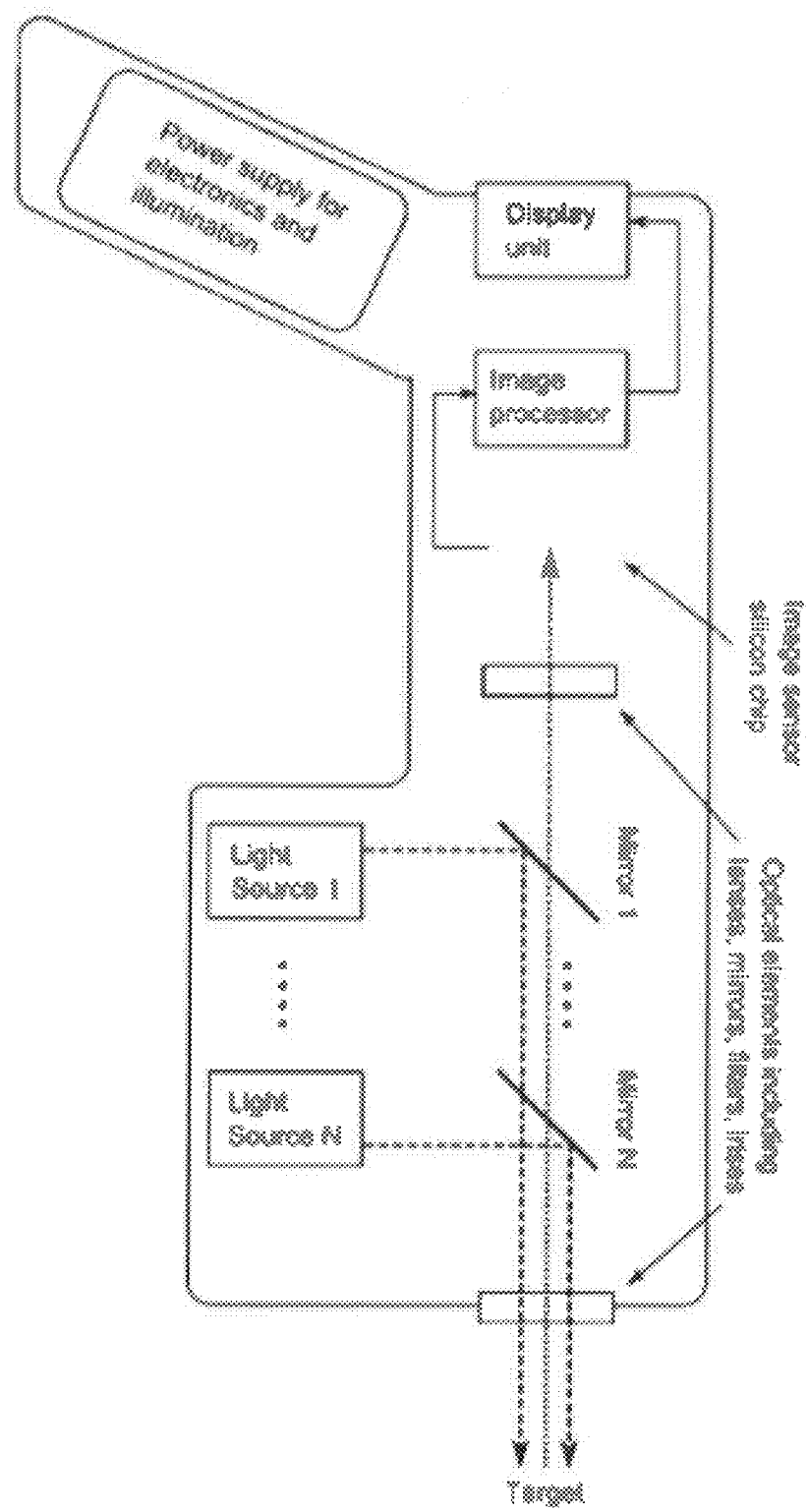

In this embodiment, data processing is done using either a computer or microcontroller or microprocessor or an equivalent electronic circuit. The acquired time-stack of 80 images is stored and a temporal laser speckle (tLS) image can be calculated using equation (1). The WL images are averaged together to obtain a basic WL image. These two images can then be combined or co-processed in any number of ways described herein, for instance to classify arterioles and venules, to classify vessels by depth, to make quantitative flow measurements, etc. The results can be displayed, for example electronically or in print. In some embodiments the entire system may be integrated into a single portable unit as shown in FIG. 2. In some embodiments the entire system may be integrated with a surgical microscope as shown in FIG. 3 for intraoperative use in the clinic. In some embodiments, the system may be linked to data transmission systems to enable transmission and sharing of images and results. The system could use waveguides or fiber optics cables to allow rearrangement of the illumination or image acquisition systems.

Generally, the present systems and methods extend the capabilities of the LSI technique in imaging vasculature. It combines LS imaging with another modality of imaging, such as white/colored light reflectance imaging or LS imaging with a laser of a different color.

Arteriole Venule Classification

Figure 4:
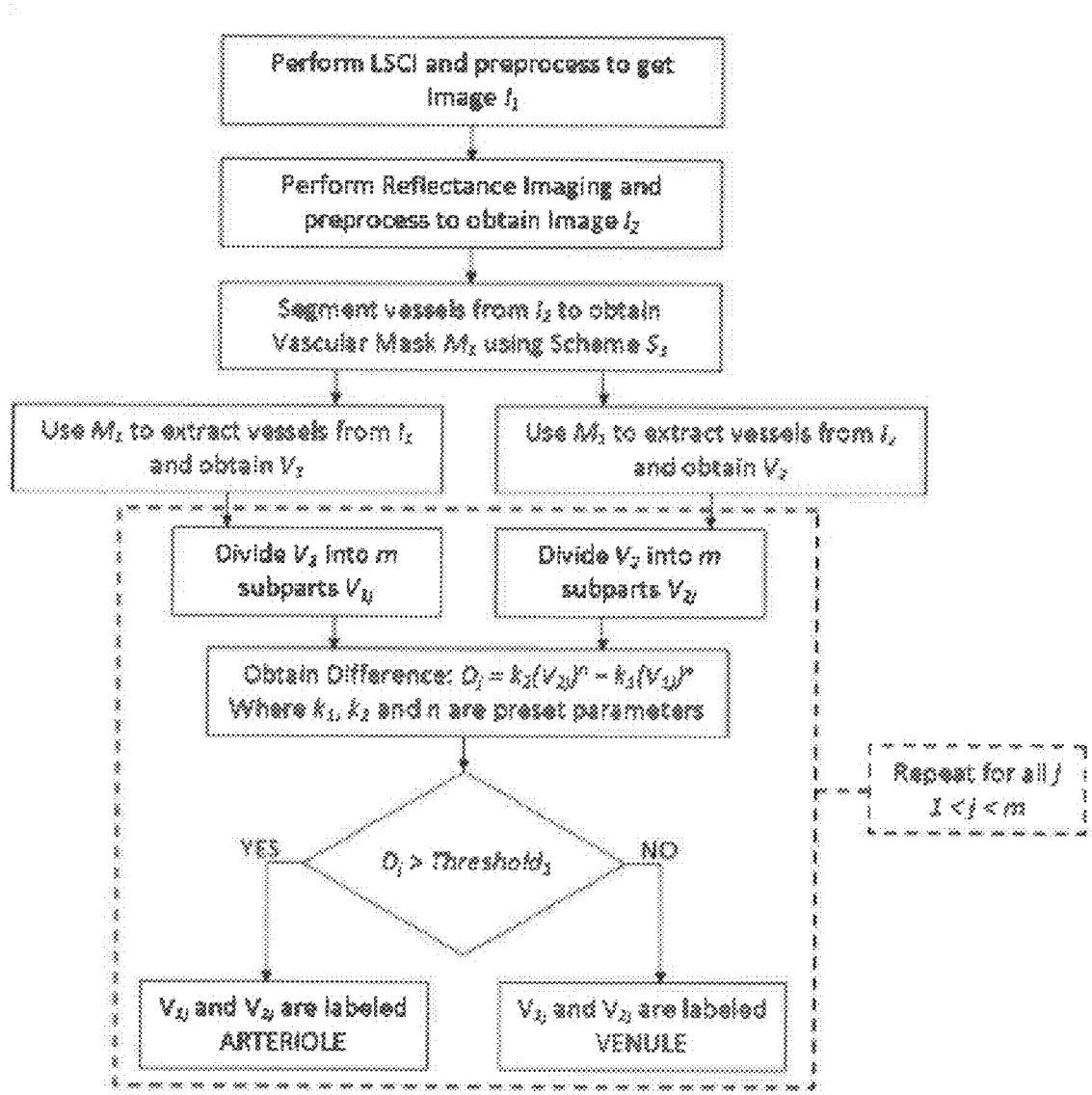
FIG. 4 shows a process for distinguishing arterioles from venules.

As shown in FIG. 4, the present systems and methods may be used to distinguish between arteries and veins (also arterioles and venules). Arterioles are identified amongst the vasculature by comparing the relative intensities of the blood vessels in the laser speckle contrast image and a second optical modality. Arterioles appear relatively darker than other vessels in LS image and relatively lighter than other vessels in the WL image. The basis of this intensity difference is that intensity contrast of a vessel compared to background tissue on a LS image is representative of the blood flow in that vessel. Thus, arterioles, which permit a higher blood flow through them than venules, appear more contrasted (or darker). However, when illuminated with white light, venules appear darker red and arterioles look brighter red due to the optical properties of de-oxygenated and oxygenated blood respectively. White light images may be captured as grey-scale maps of actual blood vessels, and hence, veins appear darker while arterioles appear fainter. FIG. 4 illustrates the method of distinguishing between arterioles and venules. This difference in laser speckle and the corresponding intensity on the white light image of blood vessels is enhanced using one of many mathematical operations ranging from digital subtraction of pixels to more complicated filters. Thus, the system and method utilize the relative appearance of the vessel in the LS contrast image and an image obtained under light from a second light source comprising one or more wavelengths at which oxygenated and deoxygenated blood have different optical properties, to determine the type of the vessel as being an arteriole or venule.

Depth Classification

The present systems and methods may be used to distinguish between surface and sub surface vessels (for example, dural vessels versus cortico-pial vessels in the brain). Multispectral laser speckle imaging may be used to achieve this. Surface vessels are identified by comparing LS images of the same region of interest acquired under sequential illumination with two different wavelengths, for example, red (632 nm) and green (532 nm). Green laser is less penetrating and only the dural vessels show up in the resulting $LS_{red}$ image, Red laser is more penetrating and thus, the LS $_{red}$ image reveals both the dural as well as sub-dural vessels. These two LS images at different wavelengths are then processed together to obtain the necessary segmentation. Detailed processing for distinguishing dural from sub-dural vessels (or more generally surface from sub-surface vessels) can be anything from simple digital subtraction to a training methodology; a function is identified in the intensity domain that identifies pixels that are darker than other vessels in $LS_{green}$ and the same pixels are approximately the same intensity as other vessels in $LS_{red}$ in a multitude of images. These pixels correspond to dural vessels. Such refinement is need-based and will depend on the problem at hand. The present methodology is generic—that of using laser speckle imaging at two or more wavelengths and comparing the images so obtained to distinguish surface from sub-surface vessels. In the eye, for example, this would permit distinguishing retinal from choroidal vessels. The specific wavelengths could be chosen differently for different applications; the penetration of red and green wavelengths works well with extraction of dural vessels from cortical vessels. Thus, the system and method utilize the relative appearance of the vessel in the LS contrast image and in a second LS contrast image obtained under coherent light from a second light source comprising a different wavelength than that of the light from the first source, to determine the location-based type of the vessel as being at two different depth levels in the same tissue or in adjacent tissues.

Multi-Exposure Laser Speckle Imaging

Figure 5:
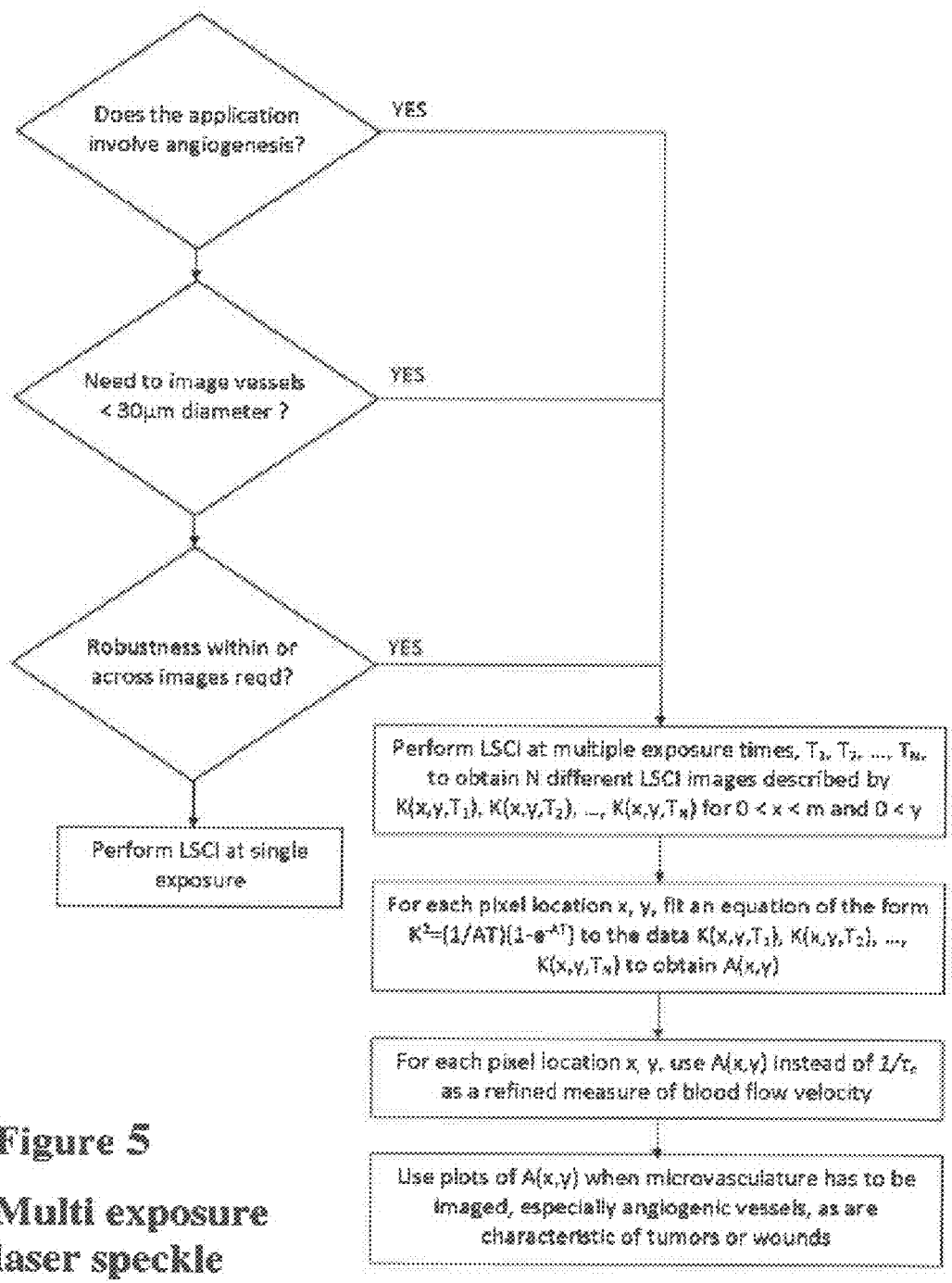
FIG. 5 shows a process for improved estimates of blood flow using multiple exposures.

As shown in FIG. 5, image acquisitions at multiple exposures may be used to produce an improved flow estimate through blood vessels. Contrast values at each exposure carry information about the flow through blood vessels at the time of the exposure. Different exposures may be acquired, and measurements of the change in contrast from one exposure to another can be used to elucidate the flow values at a pixel. This value is robust to day-to-day and preparation-related changes and thus, useful for longitudinal assessment of flow. This also helps increase the dynamic range of flow that the technique is capable of imaging. Lower flows are imaged with higher sensitivity at longer exposures. However, the sensitivity to higher flows is lost in longer exposures, as intensities saturate. Using multiple exposures can give the user the benefit of both long and short exposures. The number of exposure times used in this processing technique can be as many as 2 to 10, beyond Which the marginal utility is low. Use of multi-exposure laser speckle imaging also improves the contrast to noise ratio when imaging microvessels (vessels smaller than 30 (μm in diameter) and thus, may be used while imaging such microvessels. Angiogenesis is one condition characterized by remodeling and growth of microvessels and is therefore a promising target for imaging via the multi-exposure scheme.

Quantitative Flow Measurements

Figure 6:
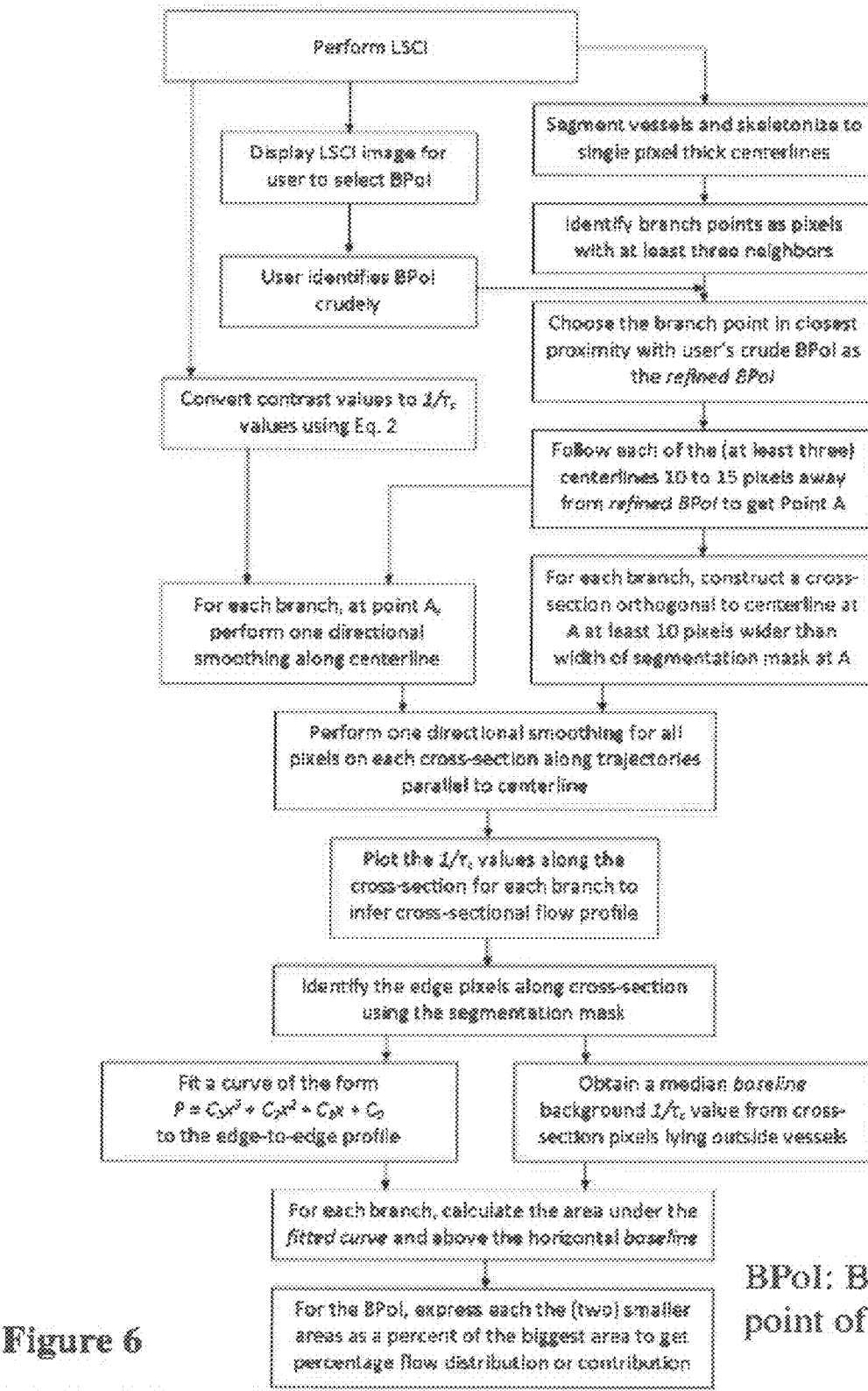
FIG. 6 shows a process for quantitatively describing blood flow within the vasculature.

The present system and methods may be used to infer the blood flow distribution in various blood vessel branches at blood vessel branch points, that is, at junctions where blood flow distributed or combines, using the methodology shown in FIG. 6. Blood vessels can be probed for laser speckle contrast values along their cross-section, converted to equivalent $1/1_c$ values as per Equation 2, and analyzed and/or plotted as a cross-sectional profile. This resulting cross-sectional profile is indicative of blood flow velocities within the vessel and can he used to estimate the blood flow through it. A secondary profile may be generated by fitting a polynomial curve through the cross-sectional profile of 1/tc values. Blood flow may be estimated as the area under the primary profile or secondary profile or a combination of the primary and secondary profiles. Similarly, blood flow may also be estimated as the volume under a surface of revolution obtained by revolving the primary profile or secondary profile or a combination of the two profiles, about the axis of the vessel. Once flow is estimated in all vessels at a junction, a percentage distribution or contribution may be inferred as the ratio of each blood flows with the maximum of the blood flows at the junction. For example, at a junction where one parent vessel bifurcates into two smaller daughter vessels, the flow in each daughter vessel may be expressed as a percentage of the flow in the parent vessel. Estimation of flow may be done at multiple junctions to infer the distribution of flow in an entire network or sub-network of connected vessel branches. Any intermediate or final result of flow calculation and percentage flow estimation may be output to the display module, or stored for subsequent use by the storage module.

Figure 7:
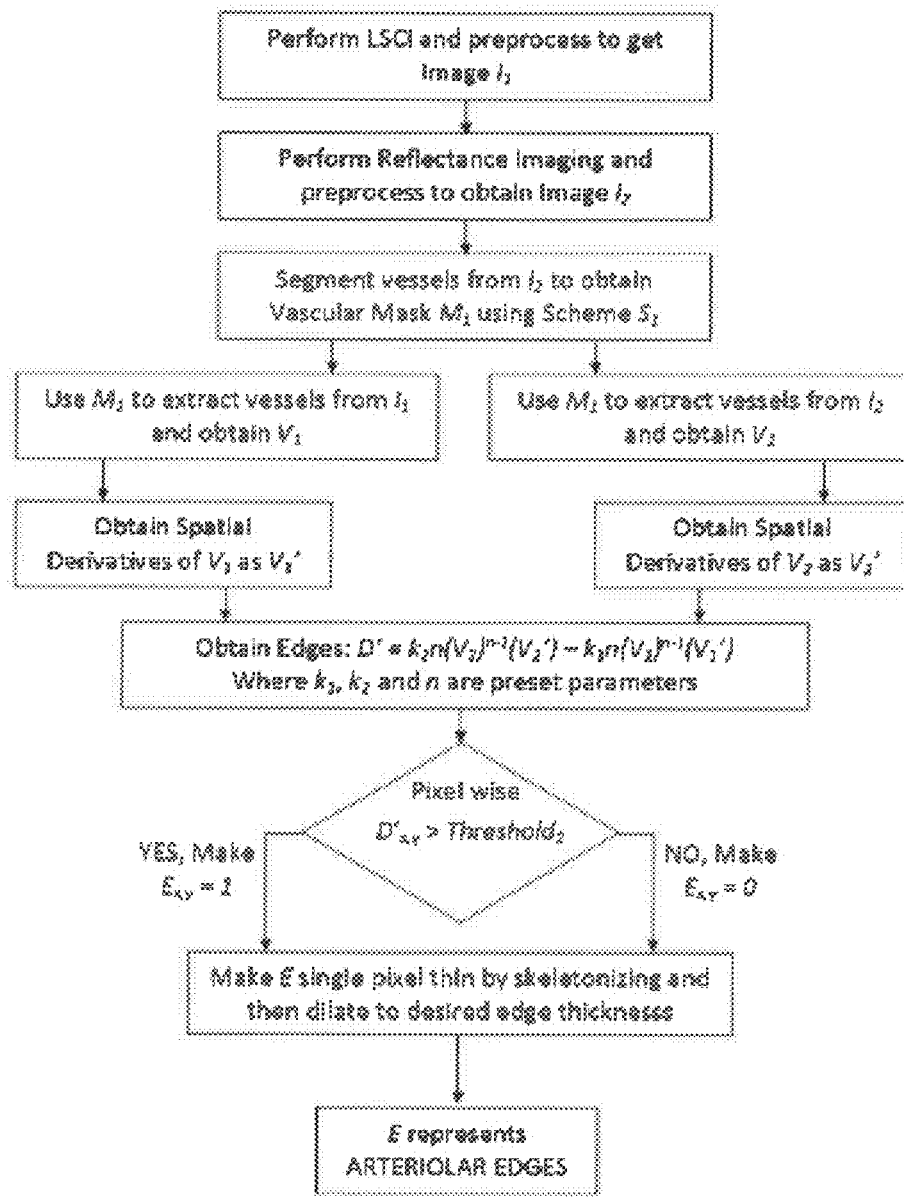
FIG. 7 shows a process for finding the edges of vessels.

An edge detection scheme may be employed to highlight the edges so determined as shown in FIG. 7. The gradient of intensity is evaluated as a first derivative and this is thresholded to identify the arterioles. A steep negative edge is encountered when passing from the background to an arteriole and a steep positive edge when passing from an arteriole to the background. While an edge may be detected while passing from a venule to the background or vice versa, setting an appropriate threshold gets rid of such false positives. It is noteworthy that the same values of thresholds apply for all the images on which the method has been used but a user may reserve the flexibility to change these thresholds. Sometimes, the gradients between pixels are steep even within an arteriole (along the cross-section) and result in internal edges. Such false positives arc removed with the consideration that an edge cannot have absolute dark pixels on both sides.

By combining some of the above features, blood flow and caliber of arterioles can be distinguished (and thus separately evaluated) from those of venules, a comparison that holds great promise in the early diagnosis of vascular and organo-vascular (for example, cerebro-vascular) disorders. To achieve this, one or more vessels of interest may be classified as arteries or veins for equivalently arterioles or venules if vessels are smaller in caliber) using the system and methods disclosed in this invention; and the flow in the same one or more vessels of interest may also be estimated using the system and methods disclosed in this invention. Accordingly, in the one or more vessels of interest, arterial flow can be distinguished from venous flow. Similarly, by utilizing both the depth classification feature and the flow estimation feature of the system and method disclosed in this invention, blood flow in vessels at different depths can be distinguished. For example, the blood supply of the dura (a surface tissue) can be distinguished from that of the brain cortex (which lies below the dura), thereby elucidating much more precise information in migraine and other neurovascular studies. Another example is discrimination of flow in retinal and choroidal vasculature.

The system can incorporate small-footprint, selectable wavelength light emitting or laser diodes for illumination. Innovative optical design reduces the number of optical components and the optical path length. Complementary metal oxide semiconductor (CMOS) image sensors, or traditional Charge Coupled Devices (CCDs), may be used for the image acquisition. CMOS imagers are approaching traditionally used CCD-based sensors in quality for high-sensitivity, low-noise imaging. In addition to being compact and low-powered, CMOS imagers offer the ability to incorporate integrated circuits on the same wafer as the image sensor. This adds image processing functions to the system at the image plane itself.

Such a system has advantages in both the clinical and research fields. In clinical scenarios, it can be used in places with little or no established infrastructure, in research scenarios, the present systems and methods will make possible a range of chronic imaging experiments from awake and behaving animal models. Current imaging techniques are limited in that they require anesthetizing or restraining the animal, thereby curtailing the range of behavioral or longitudinal experiments that can be performed.

The present systems and methods enjoy the advantages of optical imaging in being long term friendly, minimally invasive and cost effective. No external dyes are required since the contrast for laser speckle imaging is provided by moving red blood cells.

The features described above may be employed, alone or in combination, in a multitude of biomedical applications. These applications include diagnostics as well as intra and post operative monitoring. Research platforms and animal models can also benefit from the present systems and methods. Arteriole-to-venule diameter and flow ratios are valuable diagnostic and/or predictive clues in conditions such as diabetic or hypertensive retinopathies. The present systems and methods can yield such information and may be useful in assigning an early risk or late status or progress of a patient in these conditions. The present systems and methods may also help surgeons identify and quantify flow and diameter of vascular structures such as arterioles, aneurysms and arterio-venous malformations. Further, this can be done pre, intra and post operatively to assess risks and efficacies. The present systems and methods could be applied in any situation in which altered vascular diameter or flow, possibly differing between arteries and veins, or between surface and sub-surface vasculature. The target of the imaging technique is blood vessels and these imaged blood vessels could be a part of any tissue/organ including, but not limited to the brain, the eye and the skin. The imaged blood vessels could be normal (healthy) or abnormal (as in case of diseases or disorders). Abnormal vasculature occurs in cases including, but not limited to stroke, diabetic or hypertensive retinopathies, aneurysms, arteriovenous malformations, choroidal, retinal and corneal neovascularization as well as some skin diseases. The imaged blood vessels could also be newly sprouting vessels such as in case of tumors or wound healing. The imaged blood vessels could also be surgically altered, such as a clipped aneurysm or a surgical graft in case of treating Moyamoya disease.

Features of various embodiments may be combined and exchanged with one another mutatis mutandis. It is thought that the method and system of the present invention will be understood from the foregoing description and it will be apparent that various changes may be made in the form, or manufacture thereof without departing from the spirit and scope of the invention or sacrificing all of its material advantages, the form hereinbefore described being merely a preferred or exemplary embodiment thereof.

What is claimed is:

1. A system for multimodal laser speckle imaging comprising:
   a first light source positioned to emit coherent light toward a target, said coherent light having predetermined parameter(s), said parameter(s) selected from the parameter group consisting of wavelength, type of polarization, type of emission, timing of emission, pulse duration, and radiant power;
   a second light source positioned to emit either non coherent light or a second coherent light toward the target, said second coherent light having second coherent light parameter(s), said second coherent light parameter(s) selected from the parameter group consisting of wavelength, type of polarization, type of emission, timing of emission, pulse duration, and radiant power wherein said second coherent light parameter(s) is/are different than said first coherent light parameters in at least one aspect;
   wherein said coherent light and said non coherent light or second coherent light, each yield light scattered by said target, said target comprising at least one of: vasculature located within any tissue of the human or animal body, individual vessels or a network of connected vessels
   a camera positioned to receive said light scattered by said target thereby creating at least one image; and
   a processor programmed to:
      receive from the camera said at least one image of the target as illuminated by the coherent light;
      from the at least one image of the target as illuminated by the first light source, obtain a laser speckle contrast image of the target;
      receive from the camera at least one image of the target as illuminated by the second light source;
      divide the laser speckle contrast image into subparts, and divide the at least one image of the target as illuminated by the second light source into identical subparts
      determine whether each subpart includes a feature of a certain type by combining each subpart of the laser speckle contrast image with the at least one image of the target as illuminated by the second light source and comparing the combination with one or more criteria; and
      outputting the location and type of features detected in a subpart of the images.

2. A system for estimation of flow in one or more enclosed tubes having flowing particles comprising:
   a light source positioned to emit coherent light toward said target, said coherent light having predetermined parameter(s), said parameter(s) selected from the parameter group consisting of wavelength, type of polarization, type of emission, timing of emission, pulse duration, and radiant power, wherein said coherent light yields light scattered by said target;
   a camera positioned to receive said light scattered by said target thereby creating at least one image; and a processor programmed to:
receive from the camera said at least one image of the target as illuminated by the coherent light;
from the at least one image of the target as illuminated by the coherent light, obtain said laser speckle contrast image of the target;
from the at least one laser speckle contrast image of the target, obtain laser speckle contrast values and functions of laser speckle contrast values at one or more cross-sections of said tube; and
estimate flow through said tube as a function of said cross-sectional profile.

3. The system of claim 2, further comprising a display system to output one or more of the at least one raw laser speckle image, the at least one laser speckle contrast image, and the estimated flow.

4. The system of claim 2, further comprising a storage unit to store one or more of the at least one raw laser speckle image, the at least one laser speckle contrast image, and the estimated flow.

5. The system of claim 2, further comprising:
a second light source positioned to emit either non coherent light or a second coherent light toward the target, said second coherent light having second coherent light parameter(s), said second coherent light parameter(s) selected from the parameter group consisting of wavelength, type of polarization, type of emission, timing of emission, pulse duration, and radiant power wherein said second coherent light parameter(s) is/are different than said first coherent light parameters in at least one aspect.

6. The system of claim 2, wherein the processor is further programmed to quantitatively estimate blood flow in one or more blood vessels or other enclosed tubes with flowing particles comprising the steps of:
elucidation of the profile of laser speckle contrast values or blood velocity values or a parameter that is dependent on either or both of these values along a linear trajectory that traverses the cross-section of the vessel or tube;
estimation of a flow-related parameter by calculating the area or volume or both under the said profile; and
outputting the estimated flow-related parameter and the corresponding location.

7. The system of claim 2, wherein the said flow-related parameter is blood flow.

8. The system of claim 6, where the said profile is replaced by one or a combination of a secondary profile obtained by fitting a smooth curve to the data contained by the said profile,
a secondary surface obtained by rotating the said profile about an axis.

9. The system of claim 2, where estimation of blood flow is carried out in multiple blood vessels or tubes that are connected.

10. The system of claim 2, where the estimated blood flow in one vessel or tube is expressed as a percentage or ratio of the estimated blood flow in another vessel or tube.

11. The system of claim 2, where the said enclosed tubes comprise vasculature located within any tissue of the human or animal body.

12. The system of claim 2, where the estimated flow in one or more enclosed tubes is interpreted in conjunction with the type of the one or more enclosed tubes, said type comprising enclosed tube characteristics.

13. The system of claim 12, where the said type of enclosed tube comprises one of artery, arteriole, venule, or vein.

14. The system of claim 12, where the determination of said characteristics is based upon the relative appearance of said enclosed tube in the laser speckle contrast image and a second image obtained under light from a second light source; said second coherent light having second coherent light parameter(s), said second coherent light parameter(s) selected from the parameter group consisting of wavelength, type of polarization, type of emission, timing of emission, pulse duration, and radiant power wherein said second coherent light parameter(s) is/are different than said first coherent light parameters in at least one aspect.

15. A method for estimation of flow in one or more enclosed tubes having flowing particles comprising:
obtaining at least one laser speckle contrast value(s) of a target wherein said laser speckle contrast value(s) is/are obtained from a system for laser speckle imaging comprising:
a light source positioned to emit coherent light toward said target, said coherent light having predetermined parameter(s), said parameter(s) selected from the parameter group consisting of wavelength, type of polarization, type of emission, timing of emission, pulse duration, and radiant power, wherein said coherent light yields light scattered by said target;
a camera positioned to receive said light scattered by said target thereby creating at least one image; and
a processor programmed to:
receive from the camera said at least one image of the target as illuminated by the coherent light;
from the at least one image of the target as illuminated by the coherent light, obtain said laser speckle contrast image of the target;
from the at least one laser speckle contrast image of the target, obtain laser speckle contrast values and functions of laser speckle contrast values at one or more cross-sections of said tube; and
estimate flow through said tube as a function of at least one of a secondary profile obtained by fitting a smooth curve to the data contained by the said profile, or a secondary surface obtained by rotating the said profile about an axis.

16. The method of claim 15, where estimation of blood flow is carried out in multiple blood vessels or tubes that are connected.

17. The method of claim 15, where the estimated blood flow in one vessel or tube is expressed as a percentage or ratio of the estimated blood flow in another vessel or tube.

18. The method of claim 15, where the said enclosed tubes comprise vasculature located within any tissue of the human or animal body.

19. The method of claim 15, where the estimated flow in one or more enclosed tubes is interpreted in conjunction with the type of the one or more enclosed tubes, said type comprising enclosed tube characteristics.

20. The method of claim 19, where the said type of enclosed tube comprises one of artery, arteriole, venule, or vein.

21. The method of claim 19, said characteristics of enclosed tube comprising the depth dependent location of the enclosed tube in the target.

22. The system of claim 12, said characteristics comprising the depth dependent location of said enclosed tube in the target.

23. The method of claim 19, where the determination of the type of enclosed tube is made on the basis of the relative appearance of the enclosed tube in the laser speckle contrast image and a second image obtained under light from a second light source; said second coherent light having second coherent light parameter(s), said second coherent light parameter(s) selected from the parameter group consisting of wavelength, type of polarization, type of emission, timing of emission, pulse duration, and radiant power wherein said second coherent light parameter(s) is/are different than said first coherent light parameters in at least one aspect.

\* \* \* \* \*

UNITED STATES PATENT AND TRADEMARK OFFICE
CERTIFICATE OF CORRECTION

PATENT NO.         : 10,092,190 B2
APPLICATION NO.    : 14/879260
DATED              : October 9, 2018
INVENTOR(S)        : Rege et al.

Page 1 of 1

It is certified that error appears in the above-identified patent and that said Letters Patent is hereby corrected as shown below:

In the Specification

On Column 1, Line 12, before the "BACKGROUND," please insert the following paragraph:
-- STATEMENT REGARDING FEDERALLY SPONSORED RESEARCH OR DEVELOPMENT
This invention was made with government support under CA139983 and AG029681 awarded by the National Institutes of Health. The government has certain rights in the invention. --

Signed and Sealed this
Twenty-fifth Day of August, 2020

Andrei Iancu
*Director of the United States Patent and Trademark Office*